United States Patent [19]

Koga et al.

[11] 4,309,558

[45] Jan. 5, 1982

[54] METHOD FOR PRODUCING SUBSTITUTED DICHLOROSILANE

[75] Inventors: Isao Koga, Yokohamashi; Yohji Terui, Chibashi; Masuhito Ohgushi, Minamatashi, all of Japan

[73] Assignee: Chisso Corporation, Osaka, Japan

[21] Appl. No.: 72,590

[22] Filed: Sep. 5, 1979

Related U.S. Application Data

[63] Continuation-in-part of Ser. No. 884,930, Mar. 9, 1978, abandoned.

[30] Foreign Application Priority Data

Mar. 23, 1977 [JP] Japan ................... 52-31732
Mar. 23, 1977 [JP] Japan ................... 52-31733

[51] Int. Cl.³ ............................................. C07F 7/08
[52] U.S. Cl. .................................. 556/479; 556/487
[58] Field of Search ............... 260/448.2 E, 448.2 R; 556/479, 487

[56] References Cited

U.S. PATENT DOCUMENTS

| | | | |
|---|---|---|---|
| 2,476,529 | 7/1949 | Barry et al. ............... | 260/448.2 E |
| 2,698,334 | 12/1954 | Rust et al. ............... | 260/448.2 E |
| 2,907,784 | 10/1959 | Jex et al. ............... | 260/448.2 E |
| 3,159,601 | 12/1964 | Ashby ............... | 260/448.2 E X |
| 3,159,662 | 12/1964 | Ashby ............... | 260/448.2 E X |
| 3,231,594 | 1/1966 | Speier ............... | 260/448.2 E |
| 3,546,266 | 12/1970 | Coffey ............... | 556/479 X |
| 3,856,837 | 12/1974 | Chandra ............... | 260/448.2 E X |
| 3,867,343 | 2/1975 | Garden ............... | 556/479 UX |
| 3,907,850 | 9/1975 | Capka et al. ............... | 556/479 X |
| 3,907,852 | 9/1975 | Oswald et al. ............... | 260/448.2 E X |
| 4,064,154 | 12/1977 | Chandra et al. ............... | 260/448.2 E |

OTHER PUBLICATIONS

"Chemical Abstracts", 53, 21747i.

*Primary Examiner*—Paul F. Shaver
*Attorney, Agent, or Firm*—Fred Philpitt

[57] ABSTRACT

A method for producing mono-substituted dichlorosilanes selectively with a high yield from dichlorosilane is provided. According to this method, dichlorosilane and a specified compound having a double bond at α-position are reacted in the presence of a catalyst which is a homogeneous complex of ruthenium, rhodium, nickel or platinum, and a phosphine compound, or is a ruthenium chloride.

7 Claims, 4 Drawing Figures

METHOD FOR PRODUCING SUBSTITUTED DICHLOROSILANE

This application is a continuation-in-part application of Ser. No. 884,930 filed on Mar. 9, 1978, now abandoned.

DESCRIPTION OF THE INVENTION

This invention relates to a novel method for producing a mono-substituted dichlorosilane which will be referred to as $RHSiCl_2$.

With the recent development of the silicone resins industry, silicone resins having specific properties have become necessary and concurrently with this trend, monomers for silicone resins which have not been known, have now been desired. Particularly, bifunctional type monomers (which will be abbreviated to monomer) are extremely important. Those having two different organic radicals and those having a long chain organic radical, are now being desired. Accordingly, it is extremely important to prepare compounds of the type of $RHSiCl_2$ as their intermediate.

For the production of $RHSiCl_2$ a Grignard process applied between trichlorosilane ($HSiCl_3$) and $RMgX$ (wherein R is methyl, ethyl, butyl, amyl or phenyl and X is a halogen) is used but in this method, $R_xHSiCl_{3-x}$ (x is an integer of 1–3) is obtained as a mixture of three kinds of compounds, thus this method has difficulty in producing $RHSiCl_2$ alone, in the complexity of steps as well as in the danger involved in the use of a solvent such as ether or the like. It can be produced also by the side reaction of the Rochow process but has the drawback in the difficulty of separation from other products and production is limited only to those from chloride of relatively easily available hydrocarbon such as methyl group, phenyl group as R.

We have carried out intensive research works and deliberation in order to overcome these problems and found a commercially very advatageous method in which $RHSiCl_2$ is produced from dichlorosilane.

In the past, there have been made various investigations with regard to the utilization of trichlorosilane ($HSiCl_3$) but hardly any investigation has been made with regard to the utilization of dichlorosilane ($H_2SiCl_2$).

In some literatures for example Chemical Abstracts (hereinafter abbreviated to C.A.) vol. 53, p. 21747 (1959), C.A. vol 55, p. 14310 (1961), Journal of Chemical Society p. 4472 (1957) disclose the formation of $RHSiCl_2$ from dichlorosilane and an olefin (hydrosilylation of olefins with dichlorosilane) (wherein R is an organic residual group formed by combining one hydrogen atom with a molecule of olefin) but from these methods in which a chloroplatinic acid catalyst, γ-ray, ultraviolet ray, a Pt-C catalyst or the like is used, the resulting $RHSiCl_2$ is obtained only as a byproduct of $RRSiCl_2$ or a mixture with $RRSiCl_2$. Thus these methods have drawbacks that $RHSiCl_2$ cannot be obtained selectively with a good yield, separation of products is difficult, separation of catalyst after reaction is not easy, and a higher reaction temperature is necessary. Thus, it is difficult to apply these methods to a commercial production process which provides $RHSiCl_2$ alone with a good yield.

German Patent Publication No. 1942798 discloses a method wherein an organic silicon compound is produced by reacting an olefin with a silicon hydride compound in the presence of a paradium catalyts, and a reaction example of dichlorosilane is described therein, but the method is not satisfactory as a method for selectively producing $RHSiCl_2$.

Recently, silicon resins having a special property are requested by the market and monomers having different R groups in $RRSiCl_2$ become necessary and on this account, the importance of production of $RHSiCl_2$ as an intermediate of said monomer is increasing.

It is accordingly an object of the present invention to provide a method for producing selectively $RHSiCl_2$ from dichlorosilane with a higher yield which method can solve various problems in this field of art.

The present method of production of $RHSiCl_2$ comprises reacting dichlorosilane $H_2SiCl_2$ with a compound having a double bond at α-position, represented by the formula $R'R''C=CH_2$ wherein R' and R'' are hydrogen, alkyl of 1–18 carbon atoms or phenyl group and can be same or different, in the presence of a catalyst selected from the group consisting of a homogeneous complex of a transition metal (8th group metal of the periodical table) and a phosphine compound, and ruthenium chloride.

The transition metal of the homogeneous complex of a transition metal and a phosphine compound is a metal of the 8th group of the periodical table, and ruthenium, rhodium, nickel and platinum are preferable. The catalyst is a complex represented by the general formula of $MX_n(PR_3°)m$ wherein R° is phenyl (hereinafter abbreviated to Ph), aryl, alkyl or aralkyl; M is a metal selected from ruthenium, rhodium, nickel, and platinum; X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that $3 \leq n+m \leq 7$. For example, as the transition metal-phosphine compound complex, such as $RhH(PPh_3)_4$, $RhH(CO)(PPh_3)_3$, $RhCl(CO)(PPh_3)_2$, $RhCl(PPh_3)_3$, $RuCl_2(PPh_3)_3$, $RuHCl(PPh_3)_3[C_6H_6]$, $RuHCl(PPh_3)_3[C_6H_5CH_3]$, $RuH_3(PPh_3)_3[Si(OCH_3)_3]$, $RuH_3(PPh_3)_3[Si(OCH_3)_2Ph]$, $RuH(PPh_3)_3[Si(C_2H_5)_2Cl]$, $RuH_2(PPh_3)_4$, $NiCl_2(PPh_3)_2$ and $Pt(PPh_3)_4$ can be mentioned.

Further, said ruthenium chloride is preferably $RuCl_3.3H_2O$. $RuCl_3.3H_3O$ is reduced in a reaction system by ≡SiH group to form a lower valency complex (ligand is olefin or hydrosilane) and is believed to conduct a performance same with the above-mentioned complex.

As for the compound having a double bond at α-position used in the present invention, for example, ethylene, propylene, butene, pentene, hexene, octene, decene, dodecene, tetradecene, hexadecene, octadecene, styrene, α-methyl styrene and the like can be mentioned.

The reaction temperature of the production method of the present invention is in the range from room temperature to 200° C. The temperature is preferably in the range from room temperature to 150° C., most preferably in the range from room temperature to 110° C.

The reaction time can be varied in the range of 0.1–60 hours depending upon the catalyst concentration and the reaction temperature.

The reaction can be carried out under either the atmospheric pressure or a superatmospheric pressure.

The catalyst concentration is in the range of $1-10^{-15}$ mol % relative to dichlorosilane, preferably in the range from 1 to $10^{-8}$ mol %. If necessary, dichlorosilane and a compound having a double bond at α-position can be reacted in any ratio.

The production method of the present invention can be carried out by using any of the type of the apparatus of batch type, continuous type and semi-batch type. For example, there are a method in which liquefied dichlorosilane, a compound having a double bond at α-position, and a catalyst are introduced into a reactor which is then sealed and heated to effect reaction and $RHSiCl_2$ is obtained by distillation after reaction; a method in which a continuous reactor containing a catalyst solution is used and dichlorosilane and a compound having a double bond at α-position is continuously fed from one direction and a product is discharged from the other direction to feed into a distillation column, $RHSiCl_2$ is caused to flow out from the top of the column, and a catalyst solution in a still liquid state is returned to the reactor to recirculate the catalyst; and a method in which a catalyst is supported on a carrier to form a fixed layer through which dichlorosilane and a compound having a double bond at α-position are passed to effect reaction, etc.

The feature of the production method of $RHSiCl_2$ of the present invention is the fact that dichlorosilane which has hardly been heretofore used can be used as a commercial raw material by which various kinds of $RHSiCl_2$ can be produced. A further feature is the fact that $RHSiCl_2$ alone can be produced from dichlorosilane with an extremely high yield, and particularly, $RRSiCl_2$ is not produced at all at a temperature from room temperature to 110° C., i.e. reaction proceeds selectively and almost no by-product is produced. Further it has the advantages in that no catalyst separation step is necessary, $RHSiCl_2$ can be obtained by a simple distillation and a catalyst can be reused without subjecting to a purification step. Thus the present invention provides an extremely advantageous method as a commercial production method. Further, according to the method of the present invention, novel $RHSiCl_2$ such as 2-phenylethylhydrodichlorosilane and 2-phenylpropylhydrodichlorosilane can be produced.

EXAMPLE 1

Figure 1:
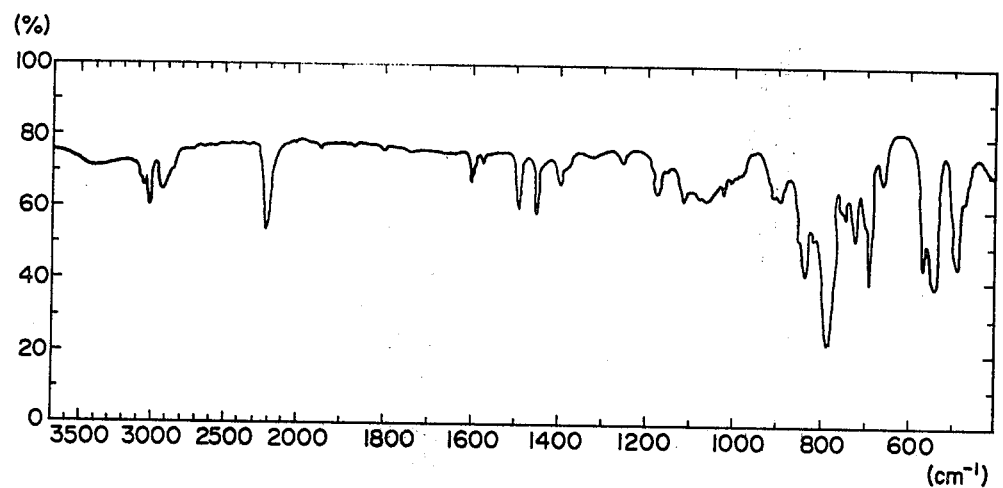
FIG. 1 shows the infrared spectra of 2-phenylethylhydrodichlorosilane.

Zero point eight nine mol of 1-hexene and 0.1 mol % (relative to dichlorosilane) of catalyst $NiCl_2(PPh_3)_2$ were introduced into a 500 ml pressure-proof stainless reactor and after closing said reactor, was cooled in a dry ice-methanol bath. After introducing 0.64 mol of dichlorosilane through an introducing pipe, the reactor was sealed and reaction was carried out with stirring in an oil bath at 110° C. for one hour to produce n-hexyldichlorosilane (n-$C_6H_{13}SiHCl_2$). After reaction, n-$C_6H_{13}SiHCl_2$ having a boiling point of 100°-102° C./100 mmHg and $n_D^{20}$ of 1.4412 was obtained by distillation. The yield was as shown in Table 1 and there was no by-product formed.

EXAMPLES 2–10

The process same with that of Example 1 was repeated by changing catalyst, temperature and time. The result thereof is shown in Table 1.

COMPARATIVE EXAMPLE 1

The process same with that of Example 2 was repeated by using a $H_2PtCl_6.6H_2O$-isopropanol solution as a catalyst. n-$C_6H_{13}SiHCl_2$ was obtained with a yield of 21% together with 79% yield of di-n-hexyldichlorosilane[(n-$C_6H_{13})_2SiCl_2$].

EXAMPLE 11

Zero point 64 mol of dichlorosilane and 1.40 mol of 1-octene and 0.05 mol % of $RhCl(PPh_3)_3$ as a catalyst (relative to dichlorosilane) were charged into a 500 ml pressure-proof stainless steel reactor as in Example 1 and sealed. Reaction was carried out by placing the reactor in an oil bath at a temperature of 100° C. for 30 hours to produce n-octyldichlorosilane (n-$C_8H_{17}SiHCl_2$). After reaction, n-$C_8H_{17}SiHCl_2$ having a boiling point of 143°-144° C./10 mmHg and $n_D^{20}$ of 1.4445 was obtained by distillation. The yield thereof was 79%. No (n-$C_8H_{17})_2SiCl_2$ and no by-product were produced.

COMPARATIVE EXAMPLE 2

By using, as a catalyst, a $H_2PtCl_6.6H_2O$-isopropanol solution and by the same operation as that of Example 11, dioctyldichlorosilane [(n-$C_8H_{17})_2SiCl_2$] was obtained with 70% yield without forming n-$C_8H_{17}SiHCl_2$.

EXAMPLE 12

Zero point five seven mol of dichlorosilane, 1.36 mol of 1-dodecene and 0.05 mol % of $RhCl(PPh_3)_3$, as a catalyst were used and the same operation was carried out as in Example 11 to produce n-dodecyl dichlorosilane (n-$C_{12}H_{25}SiHCl_2$). After the reaction, n-$C_{12}H_{25}SiHCl_2$ having a boiling point of 164°-167° C./30 mmHg and $n_D^{20}=1.4511$ was obtained by distillation. The yield thereof was 80% and no (n-$C_{12}H_{25})_2SiCl_2$ and no by-product were formed.

COMPARATIVE EXAMPLE 3

As a catalyst a $H_2PtCl_6.6H_2O$-isopropanol solution was used and the same operation was carried out as in Example 12 in other points. No n-$C_{12}H_{25}SiHCl_2$ was obtained and di-n-dodecyldichlorosilane [(n-$C_{12}H_{25})_2SiCl_2$] was obtained with 70% yield.

TABLE 1

| | | | | | Yield %* | |
| --- | --- | --- | --- | --- | --- | --- |
| Examples | Catalyst Complex compound** | mol % | Temperature (°C.) | Time (hr) | R\SiCl$_2$/H | R\SiCl$_2$/R |
| 1 | $NiCl_2(PPh_3)_2$ | 0.1 | 110 | 1 | 97 | 0 |
| 2 | $Pt(PPh_3)_4$ | 0.08 | 100 | 2 | 99 | 0 |
| 3 | $RuH_2(PPh_3)_4$ | 0.1 | 100 | 3 | 91 | 0 |
| 4 | $RuH_3(PPh_3)_3[Si(OMe)_3]$ | 0.1 | 90 | 4 | 94 | 0 |
| 5 | $RuH_3(PPh_3)_3[Si(OMe)_2Ph]$ | 0.1 | 100 | 2 | 97 | 0 |
| 6 | $RuHCl(PPh_3)_3[C_6H_6]$ | 0.1 | 120 | 15 | 99 | 1 |

TABLE 1-continued

| Examples | Catalyst Complex compound** | mol % | Temperature (°C.) | Time (hr) | Yield %* $\overset{R}{\underset{H}{\diagdown}}SiCl_2$ | Yield %* $\overset{R}{\underset{R}{\diagdown}}SiCl_2$ |
|---|---|---|---|---|---|---|
| 7 | RuCl$_2$(PPh$_3$)$_3$ | 0.1 | 120 | 15 | 96 | 1 |
| 8 | RhH(PPh$_3$)$_4$ | 0.1 | 140 | 1 | 96 | 2 |
| 9 | RhCl(CO)(PPh$_3$)$_2$ | 0.1 | 130 | 8 | 92 | 2 |
| 10 | RhCl(PPh$_3$)$_3$ | 0.1 | 100 | 1 | 99 | 0 |

*R = n-C$_6$H$_{13}$
**Me = CH$_3$

EXAMPLE 13

Fourteen point six millimol of dichlorosilane, 34.0 millimol of 1-butene, 0.8 mol % (relative to dichlorosilane) of RhCl(PPh$_3$)$_3$ as a catalyst and 1 ml of mesitylene as a solvent were introduced into a pressure-proof stainless steel reactor as in Example 1 and sealed. The reaction was carried out in an oil bath at 100° C. for 3 hours to produce n-butyldichlorosilane (n-C$_4$H$_9$SiHCl$_2$). After the reaction, 11.8 millimol of n-C$_4$H$_9$SiHCl$_2$ having a boiling point of 129°–130° C. and $n_D^{20}$ of 1.4272 was obtained by distillation with a yield of 81%. Further there was obtained no di-n-butyldichlorosilane.

EXAMPLE 14

Fifty six point 4 millimol of dichlorosilane, 57.7 millimol of 1-octadecene and 0.07 mol % (relative to dichlorosilane) of RhCl(PPh$_3$)$_3$ as a catalyst were introduced into a pressure-proof stainless steel reactor as in Example 1 and sealed. Reaction was carried out in an oil bath at 130° C. for 25 hours to produce n-octadecyldichlorosilane (n-C$_{18}$H$_{37}$SiHCl$_2$). After reaction, 47.9 millimol of n-C$_{18}$H$_{37}$SiHCl$_2$ having a boiling point of 187°–188.5° C./2 mmHg and $n_D^{20}$ of 1.4599 was obtained by vacuum distillation. Its yield was 85%. Further there was obtained no di-n-octadecyldichlorosilane.

EXAMPLE 15

To a stainless steel reactor, 0.03 mol of dichlorosilane, 0.06 mol of isobutene and 0.12 mol % (relative to dichlorosilane) of RhCl(PPh$_3$)$_3$ as a catalyst and 1 ml of mesitylene as a solvent were introduced and sealed as in Example 1. Reaction was carried out in an oil bath at 100° C. for 20 hours to produce isobutyldichlorosilane [(CH$_3$)$_2$CHCH$_2$SiHCl$_2$]. After reaction, 0.024 mol of (CH$_3$)$_2$CHCH$_2$SiHCl$_2$ having a boiling point of 120°–130° C. was obtained by distillation with a yield of 80%.

EXAMPLE 16–18

The process same with that of Example 1 was carried out by changing catalyst, temperature and time. The result is shown in Table 2.

TABLE 2

| Examples | Catalyst Complex compound | mol % | Temperature (°C.) | Time (hr) | Yield %* $\overset{R}{\underset{H}{\diagdown}}SiCl_2$ | Yield %* $\overset{R}{\underset{R}{\diagdown}}SiCl_2$ |
|---|---|---|---|---|---|---|
| 16 | RuH$_2$(PPh$_3$)$_4$ | 0.1 | 70 | 25 | 91 | 0 |
| 17 | RhCl(PPh$_3$)$_3$ | 0.1 | 70 | 15 | 99 | 0 |
| 18 | Pt(PPh$_3$)$_4$ | 0.08 | 70 | 25 | 99 | 0 |

*R = n-C$_6$H$_{13}$

EXAMPLE 19

To a 500 ml pressure-proof stainless steel reactor, 0.61 mol of dichlorosilane, 0.84 mol of 1-hexene and 0.2 mol % (relative to dichlorosilane) of RuCl$_3$.3H$_2$O as a catalyst were charged as in Example 1 and sealed. Reaction was carried out by placing the reactor in an oil bath at a temperature of 80° C. for 7 hours to produce n-hexyldichlorosilane [n-C$_6$H$_{13}$HSiCl$_2$]. After reaction, n-C$_6$H$_{13}$HSiCl$_2$ having a boiling point of 100°–102° C./100 mmHg was obtained by distillation with a yield of 99%. No di-n-hexyldichlorosilane [(n-C$_6$H$_{13}$)$_2$SiCl$_2$] was formed.

EXAMPLE 20

A process same with that of Example 19 was carried out except that 0.08 mol % of a catalyst was used. The yield of n-C$_6$H$_{13}$HSiCl$_2$ was 98%. No (n-C$_6$H$_{13}$)$_2$SiCl$_2$ was formed.

COMPARATIVE EXAMPLE 4

A process same with that of Example 20 was carried out except that RuCl$_3$.3H$_2$O was replaced by a H$_2$PtCl$_6$.6H$_2$O-isopropanol solution. There were obtained n-C$_6$H$_{13}$HSiCl$_2$ with 20% yield and (n-C$_6$H$_{13}$)$_2$SiCl$_2$ with 80% yield.

COMPARATIVE EXAMPLE 5

The same process was carried out as in Example 19 except that RuCl$_3$.3H$_2$O was replaced by RhCl$_3$.3H$_2$O. There was obtained n-C$_6$H$_{13}$HSiCl$_2$ with 9% yield and (n-C$_6$H$_{13}$)$_2$SiCl$_2$ was not obtained.

COMPARATIVE EXAMPLE 6

The same process was carried out as in Example 20 except that RuCl$_3$.3H$_2$O was replaced by PdCl$_2$. There was obtained no product.

EXAMPLE 21

Five point three five gram of dichlorosilane (53.0 millimol), 5.70 g of styrene (54.7 millimol) and as a catalyst, 0.0490 g of RhCl(PPh$_3$)$_3$ (5.3 × 10$^{-5}$ mol) were charged in a stainless steel reaction tube and after sealing, reaction was carried out by placing in an oil bath at 80° C. for 20 hours and then reacted solution was subjected to vacuum distillation to produce 9.5 g (46.3 millimol) of product of [2-phenylethylhydrodichlorosilane] having a boiling point of 76°–77° C./3 mmHg and $n_D^{20}$ of 1.5199.

Figure 2:
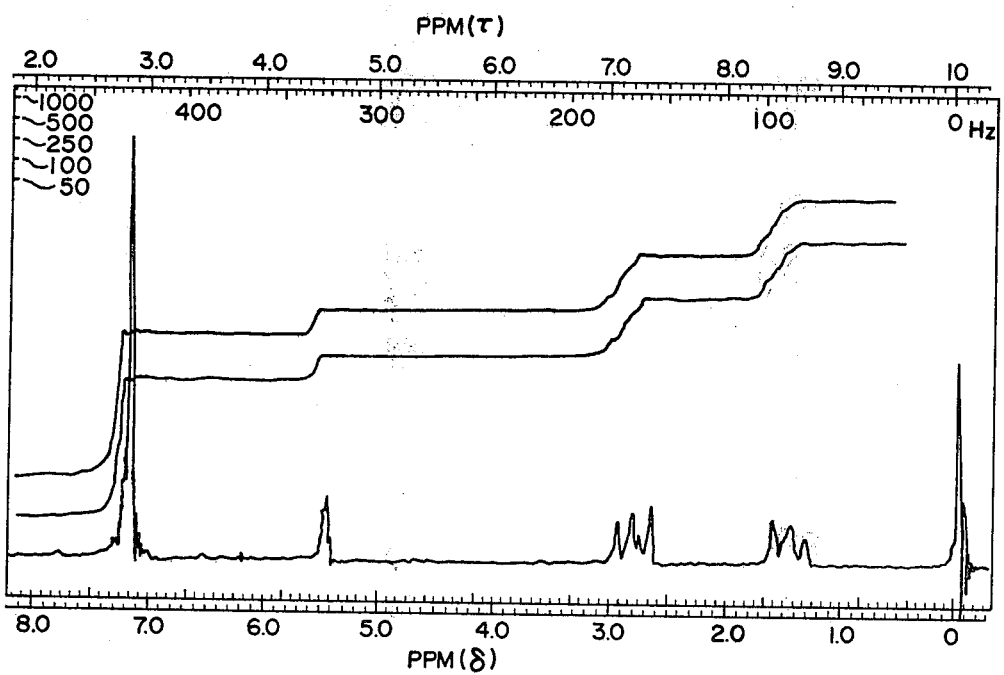
FIG. 2 shows its NMR spectra.

The infrared spectrum of this product is shown in FIG. 1 indicating a characteristic absorption of Si—H at 2206 cm$^{-1}$ and the NMR spectrum of this product is shown in FIG. 2 indicating the signals of protons of Si—H, Si—CH$_2$, Ph—CH$_2$, and Ph— at peaks of 5.52 ppm, 1.53 ppm, 2.88 ppm and 7.22 ppm, respectively.

From the above-mentioned result, it has been confirmed that the product is a compound represented by the formula [C$_6$H$_5$CH$_2$CH$_2$SiHCl$_2$].

EXAMPLE 22

Five point three five gram (53.0 millimol) of dichlorosilane, 6.30 g (53.0 millimol) of α-methylstyrene and as a catalyst, 0.0502 g (5.43×10$^{-5}$ mol) of RhCl(PPh$_3$)$_3$ were charged in a stainless steel reaction tube. After sealing, reaction was carried out by placing it and heating in an oil bath at 100° C. for 15 hours. After reaction, reacted solution was subjected to vacuum distillation to give 9.0 g (41.1 millimol) of product of [2-phenylpropylhydrodichlorosilane] having a b.p. of 108°–109° C./5 mmHg and n$_D^{20}$ of 1.5149.

Figure 3:
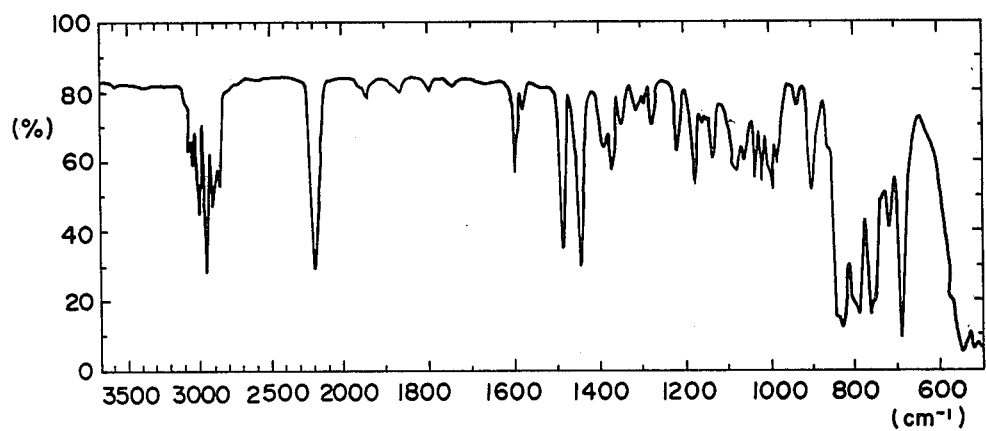
FIG. 3 shows the infrared spectra of 2-phenylpropylhydrodichlorosilane.
Figure 4:
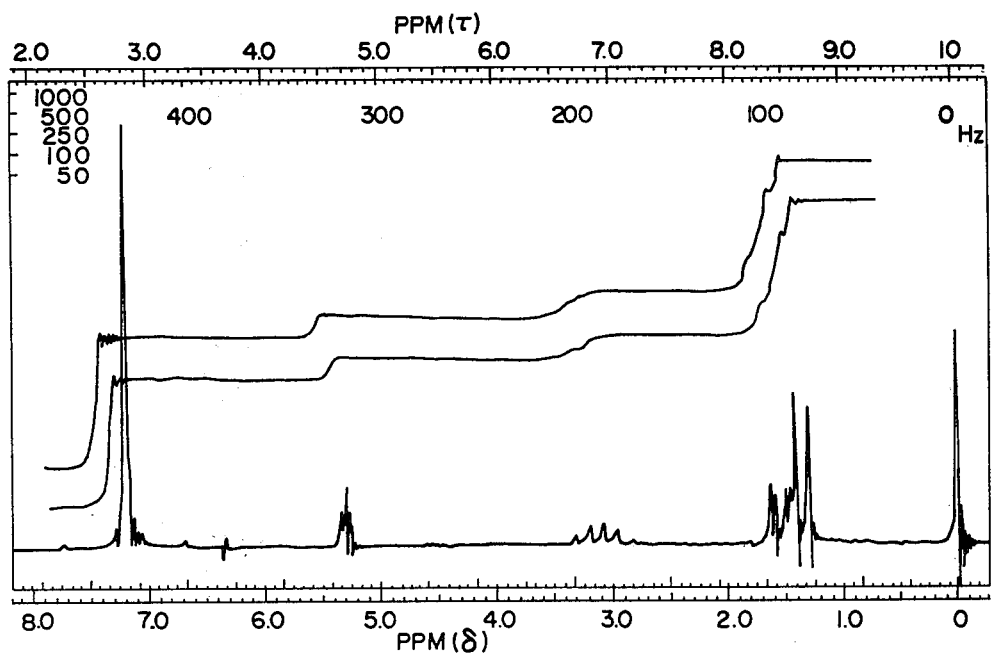
FIG. 4 shows its NMR spectra.

The infrared spectrum of this product is shown in FIG. 3 indicating a characteristic absorption of Si—H at 2205 cm$^{-1}$. The NMR spectrum thereof is shown in FIG. 4, indicating the peaks at 5.28 ppm, 1.54 ppm, 3.13 ppm, 1.35 ppm and 7.19 ppm corresponding to the signals of protons of

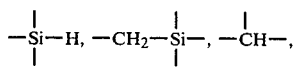

—CH$_3$ and —C$_6$H$_5$, respectively.

From the above-mentioned result, it has been confirmed that the product is a compound represented by the formula [C$_6$H$_5$CHCH$_3$CH$_2$SiHCl$_2$].

COMPARATIVE EXAMPLES 7-9

Experiments were carried out in the same manner as in Example 1, but employing Pd(PPh$_3$)$_4$ and PdCl$_2$(PPh$_3$)$_2$ and varying temperature and time. The results are shown in Table 3.

TABLE 3

| Comparative examples | Catalyst Complex compound | Mol % | Temperature (°C.) | Time (hr) | Yield %* R$\diagdown$SiCl$_2$ H$\diagup$ | R$\diagdown$SiCl$_2$ R$\diagup$ |
|---|---|---|---|---|---|---|
| 7 | Pd(PPh$_3$)$_4$ | 0.1 | 125 | 15 | 42 | 8 |
| 8 | PdCl$_2$(PPh$_3$)$_2$ | 0.1 | 125 | 15 | 34 | 5 |
| 9 | PdCl$_2$(PPh$_3$)$_2$ | 0.1 | 170 | 15 | 91 | 6 |

*R = n-C$_6$H$_{13}$

What is claimed is:

1. A method for producing a mono-substituted dichlorosilane which comprises reacting dichlorosilane H$_2$SiCl$_2$ with a vinylidene compound represented by the general formula R$^1$R$^2$C=CH$_2$ (wherein R$^1$ and R$^2$ are each hydrogen, an alkyl group of 1-18 carbon atoms or a phenyl group and are the same or different) in the presence of a catalyst which is a homogeneous complex represented by the general formula MX$_n$(PR°$_3$)$_m$ wherein R° is aryl, alkyl or aralkyl; M is ruthenium; X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that 3≦(n+m)≦7 to give a compound of the general formula R$^1$R$^2$CHCH$_2$SiHCl$_2$.

2. A method according to claim 1 wherein the complex is RuCl$_2$(PPh$_3$)$_3$, RuHCl(PPh$_3$)$_3$, RuHCl(PPh$_3$)$_3$[C$_6$H$_6$], RuHCl(PPh$_3$)$_3$[C$_6$H$_5$CH$_3$], RuH$_3$(PPh$_3$)$_3$[Si(OCH$_3$)$_3$], RuH$_3$(PPh$_3$)$_3$[Si)OCH$_3$)$_2$Ph], RuH(PPh$_3$)$_3$-[Si(C$_2$H$_5$)$_2$Cl], or RuH$_2$(PPh$_3$)$_4$.

3. A method for producing a monosubstituted dichlorosilane which comprises reacting dichlorosilane H$_2$SiCl$_2$ with a vinylidene compound represented by the general formula R$^1$R$^2$C=CH$_2$ (wherein R$^1$ and R$^2$ are each hydrogen, an alkyl group of 1-18 carbon atoms or a phenyl group and are the same or different) in the presence of a catalyst which is a homogeneous complex represented by the general formula MX$_n$(PR°$_3$)$_m$ wherein R° is aryl, alkyl or aralkyl; M is platinum X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that 3≦(n+m)≦7 to give a compound of the general formula R$^1$R$^2$CHCH$_2$SiHCl$_2$.

4. A method according to claim 3 wherein the complex is Pt(PPh$_3$)$_4$.

5. A method for producing a mono-substituted dichlorosilane which comprises reacting dichlorosilane H$_2$SiCl$_2$ with a vinylidene compound represented by the general formula R$^1$R$^2$C=CH$_2$ (wherein R$^1$ and R$^2$ are each hydrogen, an alkyl group of 1-18 carbon atoms or a phenyl group and are the same or different in the presence of a catalyst which is RuCl$_3$.3H$_2$O to give a compound of the general formula R$^1$R$^2$CHCH$_2$SiHCl$_2$.

6. A method of producing 2-phenylethylhydrodichlorosilane which comprises reacting dichlorosilane with styrene in the presence of a catalyst which is a homogeneous complex represented by the general formula MX$_n$(PR°$_3$)$_m$ wherein R° is aryl, alkyl or aralkyl; M is rhodium, X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that 3≦(n+m)≦7.

7. A method for producing 2-phenylpropylhydrodichlorosilane which comprises reacting dichlorosilane with α-methyl styrene in the presence of a catalyst which is a homogeneous complex represented by the general formula MX$_n$(PR°$_3$)$_m$ wherein R° is aryl, alkyl or aralkyl; M is rhodium, X is a covalently bound halogen or hydrogen atom, a covalently bound substituted silyl group, or a non-covalently bound carbon monoxide molecule or aromatic hydrocarbon compound; and n is an integer of 0 to 4 and m is an integer of 2 to 4 provided that 3≦(n+m)≦7.

* * * * *